US011959068B2

(12) United States Patent
Manna et al.

(10) Patent No.: US 11,959,068 B2
(45) Date of Patent: Apr. 16, 2024

(54) COMPOSITIONS AND METHODS FOR REMEDIATION OF SULFATE REDUCING PROKARYOTES

(71) Applicant: Lanxess Corporation, Pittsburg, PA (US)

(72) Inventors: Kathleen Manna, Collegeville, PA (US); Ian A. Tomlinson, Midland, MI (US); Abhiram Thatipelli, College Station, TX (US); Christopher Janes, College Station, TX (US); Elizabeth J. Summer, College Station, TX (US)

(73) Assignee: Lanxess Corporation, Pittsburg, PA (US)

( * ) Notice: Subject to any disclaimer, the term of this patent is extended or adjusted under 35 U.S.C. 154(b) by 0 days.

(21) Appl. No.: 18/160,867

(22) Filed: Jan. 27, 2023

(65) Prior Publication Data

US 2023/0227772 A1  Jul. 20, 2023

Related U.S. Application Data

(62) Division of application No. 16/630,201, filed as application No. PCT/US2018/041066 on Jul. 6, 2018, now Pat. No. 11,584,915.

(60) Provisional application No. 62/531,568, filed on Jul. 12, 2017.

(51) Int. Cl.
| | |
|---|---|
| *C12N 1/20* | (2006.01) |
| *A01N 63/27* | (2020.01) |
| *A01N 63/50* | (2020.01) |
| *C02F 1/50* | (2023.01) |
| *C02F 3/34* | (2023.01) |
| *C02F 103/10* | (2006.01) |
| *C07K 14/21* | (2006.01) |
| *C09K 8/582* | (2006.01) |
| *C12R 1/385* | (2006.01) |

(52) U.S. Cl.
CPC ............ *C12N 1/205* (2021.05); *A01N 63/27* (2020.01); *A01N 63/50* (2020.01); *C02F 1/50* (2013.01); *C02F 3/34* (2013.01); *C07K 14/21* (2013.01); *C09K 8/582* (2013.01); *C02F 2103/10* (2013.01); *C02F 2303/04* (2013.01); *C12R 2001/385* (2021.05)

(58) Field of Classification Search
None
See application file for complete search history.

(56) References Cited

U.S. PATENT DOCUMENTS

| | | | |
|---|---|---|---|
| 6,551,795 B1 | 4/2003 | Rubenfield et al. | |
| 7,052,901 B2* | 5/2006 | Crews | C09K 8/605 435/281 |
| 2008/0113406 A1 | 5/2008 | Martin et al. | |
| 2008/0286236 A1 | 11/2008 | Gebhart et al. | |
| 2012/0214713 A1* | 8/2012 | Mu | C12N 1/36 507/201 |
| 2012/0277126 A1* | 11/2012 | Fallon | C09K 8/582 507/201 |
| 2014/0315765 A1* | 10/2014 | McDaniel | C09K 8/68 507/201 |
| 2015/0259642 A1* | 9/2015 | Sangwai | C09K 8/52 435/253.3 |
| 2015/0352610 A1* | 12/2015 | Carpenter | B09C 1/10 405/128.75 |

FOREIGN PATENT DOCUMENTS

| | | |
|---|---|---|
| WO | WO 2012/064660 | 5/2012 |
| WO | WO 2016/081239 | 5/2016 |
| WO | WO 2019/014061 | 1/2019 |

OTHER PUBLICATIONS

Nakayama, K. et al. "The R-Type pyocin of Pseudomonas aeruginosa is related to P2 phage, and the F-type is related to lambda phage" Molecular Microbiology, vol. 38, No. 2. Oct. 1, 2000. pp. 213-231.
International Search Report and Written Opinion, dated Oct. 9, 2018 in corresponding International Patent Application PCT/US2018/041066, filed Jul. 6, 2018.
Communication Under Rules 161(1) and 162 EPC issued in corresponding European Patent Application No. 18746411, dated Feb. 19, 2020.
Response to Communication filed in European Patent Application No. 18746411, filed Aug. 26, 2020.
Communication Pursuant to Article 94(3) EPC issued in corresponding European Patent Application No. 18746411, dated May 24, 2022.
Response to Communication filed in European Patent Application No. 18746411, filed Sep. 29, 2022.
Restriction Requirement dated Jun. 10, 2021 issued on U.S. Appl. No. 16/630,201.
Response to Restriction Requirement filed in U.S. Appl. No. 16/630,201, filed Nov. 10, 2021.
Non-Final Office Action dated Jan. 21, 2022 issued on U.S. Appl. No. 16/630,201.
Response to Non-Final Office Action filed in U.S. Appl. No. 16/630,201, filed Jul. 22, 2022.

* cited by examiner

*Primary Examiner* — John J Figueroa
(74) *Attorney, Agent, or Firm* — Howson & Howson, LLP; Colleen M. Schaller

(57) ABSTRACT

Compositions and methods are provided for use in controlling souring and corrosion causing prokaryotes, such as SRP, by treating oil and gas field environments or treatment fluids with a newly identified bacterial strain ATCC Accession No. PTA-124262 as a self-propagating whole cell that produces an anti-SRP bacteriocin in situ. In another aspect, the methods use one or more toxic peptides or proteins isolated therefrom in methods to control unwanted prokaryotic growth in these environments.

11 Claims, No Drawings
Specification includes a Sequence Listing.

SEQUENCE LISTING

```
Sequence total quantity: 4
SEQ ID NO: 1            moltype = AA  length = 177
FEATURE                 Location/Qualifiers
source                  1..177
                        mol_type = protein
                        organism = Pseudomonas aeruginosa
SEQUENCE: 1
MSSRLLPPNR SSLERSLGDV LPAELPVPLR ELNDPARCEA ALLPYLAWTR SVDRWDPDWS   60
DEAKRNAVAT SFVLHQRKGT LTALRQVVEP IGALSEVTEW WQRSPLGVPG TFEITVDVSD  120
RGIDEGTVLE LERLLDDVRP VSRHLTRLDL RITPVIRSRH GLAVTDGDTL EIFPWKQ     177

SEQ ID NO: 2            moltype = AA  length = 701
FEATURE                 Location/Qualifiers
source                  1..701
                        mol_type = protein
                        organism = Pseudomonas aeruginosa
SEQUENCE: 2
MTTNTPKYGG LLTDIGAAAL AAASAAGKKW QPTHMLIGDA GGAPGDTPDP LPSAAQKSLI   60
NQRHRAQLNR LFVSDKNANT LVAEVVLPVE VGGFWIREIG LQDADGKFVA VSNCPPSYKA  120
AMESGSARTQ TIRVNIALSG LENVQLLIDN GIIYATQDWV KEKVAADFKG RKILAGNGLV  180
GGGDLSADRS IGLAPSGVTA GSYRSVTVNA NGVVTQGSNP TTLAGYAIGD AYTKADTDGK  240
LAQKANKATT LAGYGITDAL RVDGNAVSSS RLAAPRSLAA SGDASWSVTF DGSANVSAPL  300
SLSATGVAAG SYPKVTVDTK GRVTAGMALA ATDIPGLDAS KLVSGVLAEQ RLPVFARGLA  360
```

```
TAVSNSSDPN  TATVPLMLTN  HANGPVAGRY  FYIQSMFYPD  QNGNASQIAT  SYNATSEMYV  420
RVSYAANPSI  REWLPWQRCD  IGGSFTKTTD  GSIGNGVNIN  SFVNSGWWLQ  STSEWAAGGA  480
NYPVGLAGLL  IVYRAHADHI  YQTYVTLNGS  TYSRCCYAGS  WRPWRQNWDD  GNFDPASYLP  540
KAGFTWAALP  GKPATFPPSG  HNHDTSQITS  GILPLARGGL  GANTAAGARN  NIGAGVPATA  600
SRALNGWWKD  NDTGLIVQWM  QVNVGDHPGG  IIDRTLTFPI  AFPSACLHVV  PTVKEVGRPA  660
TSASTVTVAD  VSVSNTGCVI  VSSEYYGLAQ  NYGIRVMAIG  Y                       701

SEQ ID NO: 3              moltype = AA  length = 386
FEATURE                   Location/Qualifiers
source                    1..386
                          mol_type = protein
                          organism = Pseudomonas aeruginosa
SEQUENCE: 3
MSFFHGVTVT  NVDIGARTIA  LPASSVIGLC  DVFTPGAQAS  AKPNVPVLLT  SKKDAAAAFG  60
IGSSIYLACE  AIYNRAQAVI  VAVGVEAAET  PEAQASAVIG  GVSAAGERTG  LQALLDGKSR  120
FNAQPRLLVA  PGHSAQQAVA  TAMDGLAEKL  RAIAILDGPN  STDEAAVAYA  KNFGSKRLFM  180
VDPGVQVWDS  ATNAARNAPA  SAYAAGLFAW  TDAEYGFWSS  PSNKEIKGVT  GTSRPVEFLD  240
GDETCRANLL  NNANIATIIR  DDGYRLWGNR  TLSSDSKWAF  VTRVRTMDLV  MDAILAGHKW  300
AVDRGITKTY  VKDVTEGLRA  FMRDLKNQGA  VINFEVYADP  DLNSASQLAQ  GKVYWNIRFT  360
DVPPAENPNF  RVEVTDQWLT  EVLDVA                                          386

SEQ ID NO: 4              moltype = AA  length = 167
FEATURE                   Location/Qualifiers
source                    1..167
                          mol_type = protein
                          organism = Pseudomonas aeruginosa
SEQUENCE: 4
MIPQTLTNTN  LFIDGVSFAG  DVPSLTLPKL  AVKTEQYRAG  GMDAPVSIDM  GLEAMEAKFS  60
TNGARREALN  FFGLADQSAF  NGVFRGSFKG  QKGASVPVVA  TLRGLLKEVD  PGDWKAGEKA  120
EFKYAVAVSY  YKLEVDGREV  YEIDPVNGVR  AINGVDQLAG  MRNDLGL                 167
```

COMPOSITIONS AND METHODS FOR REMEDIATION OF SULFATE REDUCING PROKARYOTES

RELATED PATENT APPLICATIONS

This patent application is a divisional application of U.S. application Ser. No. 16/630,201, filed on Jan. 10, 2020, which is a § 371 of International Application No. PCT/US2018/041066, filed Jul. 6, 2018, which claims the benefit of U.S. Provisional Patent Application No. 62/531,568, filed Jul. 12, 2017. The entire content of the foregoing applications is incorporated herein by reference, including all text, tables, drawings, and sequences.

DEPOSITED BIOLOGICAL MATERIAL

A novel *Pseudomonas aeruginosa* bacterial strain was deposited under the Budapest Treaty on the International Recognition of the Deposit of Material for the Purposes of Patent Procedure on Jun. 28, 2017 with the American Type Culture Collection, 10801 University Boulevard, Manassas, Virginia, 20110, USA and assigned Accession No. PTA-124262. This deposit is discussed herein.

INCORPORATION-BY REFERENCE OF MATERIAL SUBMITTED IN ELECTRONIC FORM

Applicant hereby incorporates by reference the Sequence Listing material filed in electronic form herewith. This file is labeled "80935-USC1.xml", was created on Jan. 27, 2023, and is bytes in size.

BACKGROUND OF THE INVENTION

Microbiologically influenced corrosion (MIC) and souring are primary mechanisms for degradation of infrastructure and deterioration of product quality in oil and gas operations. Considerable microbial population diversity exists in different oil and gas production environments, particularly water-containing (i.e., aqueous) environments. Sulfate reducing prokaryotes (SRPs) are single-celled organisms that do not have a nucleus or any other membrane-bound organelles, e.g., bacteria, cyanobacteria, and archaea. Various SRP species of *Desulfovibrio* are a primary causative agent of souring and MIC, because SRPs consume hydrogen, produce corrosive hydrogen sulfide, and induce formation of ferrous sulfide. Iron-reducing bacteria (IRB), such as *Shewanella oneidensis* and *Geobacter sulfurreducens*, promote corrosion by reductively dissolving the protective ferric oxide coat that forms on the steel surface. Other reported microorganisms associated with corrosion include acid-producing bacteria (APB), such as *Acetobacterium carbinolicum*, that produce corrosive acids, such as acetate and butyrate, to induce corrosion. Still other unwanted microorganisms in this environment include methane-producing archaea, such as *Methanoplanus petrolearius*. The oil and gas industry currently uses a host of biocides to treat microorganisms that cause corrosion and souring. Both oxidizing (chlorine, chloramines) or non-oxidizing chemical biocides (amine-type compounds, anthraquinones and aldehydes) are widely applied within the industry to control microbial populations. Biocide application is not always effective, possibly due to the different identities and physiologies of microorganisms to be controlled in different systems. In addition to their poor effectiveness, the environmental impacts of those chemical biocides are generally considered negative.

Some bacterial strains indigenous to oil fields produce natural antimicrobial substances to combat different surrounding oil field microbial populations. These antimicrobial substances are usually small molecules, including but not limited to bacteriocins, secreted enzymes such as proteases, RNA-degrading enzymes or cell wall lytic enzymes. Some of these substances are active only against the same or closely related species while others have a broad activity spectrum. See, e.g., US published patent application No. 2014/0090833 which describes applying a range of purified bacteriocins and International Application No. WO2016/081239. For example, some *Bacillus* strains were isolated from oil fields and their capabilities for producing antimicrobial substances against other *Bacillus* strains and SRPs were reported (Korenblum E, et al. 2005 Production of antimicrobial substances by *Bacillus subtilis* LFE-1, *B. firmus* HO-1 and *B. licheniformis* T6-5 isolated from an oil reservoir in Brazil. *J Appl Microbiol.*; 98(3):667-75).

The problems and need for remediation of SRPs in oil and gas operation waters and in oil and gas reservoirs (production of hydrogen sulfide) are well described in U.S. Pat. Nos. 8,168,419 and 8,252,576, the disclosures of which are incorporated herein by reference. See, also, Australian patent publication 2009356541 and Chinese Application No. 105154464.

A continuing need in the art exists for less toxic and more effective tools and methods for controlling microbial influenced corrosion and souring of oil and gas fields.

SUMMARY OF THE INVENTION

In one embodiment, an isolated *Pseudomonas aeruginosa* bacterium, ATCC Accession No. PTA-124262 and progeny or derivatives thereof is provided.

In another aspect, a composition having broad range killing activity against SRPs comprising *Pseudomonas aeruginosa* bacterium, ATCC Accession No. PTA-124262 and progeny or derivatives thereof and a suitable carrier.

In another aspect, a bacteriocin isolated from *Pseudomonas aeruginosa* bacterium, ATCC Accession No. PTA-124262 and progeny or derivatives thereof is provided.

In still another aspect, a composition comprises a bacteriocin isolated from *Pseudomonas aeruginosa* bacterium, ATCC Accession No. PTA-124262 and progeny or derivatives thereof and a suitable carrier.

In a further aspect, a method of controlling unwanted prokaryotes in an oil or gas field environment or treatment fluid comprises contacting the environment or fluid with an amount of *Pseudomonas aeruginosa* bacterium, ATCC Accession No. PTA-124262 and progeny or derivatives thereof effective to produce bacteriocin in situ virulent for the unwanted prokaryotes, e.g., bacteria.

In yet another aspect, a method of controlling unwanted prokaryotes in an oil or gas field environment or treatment fluid comprises contacting the environment or fluid with an effective amount of a bacteriocin isolated from *Pseudomonas aeruginosa* bacterium, ATCC Accession No. PTA-124262 and progeny or derivatives thereof, wherein said bacteriocin is virulent for the unwanted prokaryotes, e.g., bacteria.

In yet another aspect, a method of controlling unwanted prokaryotes in an oil or gas field environment or treatment fluid involves adding to said environment or fluid an effective amount of the whole cell bacterium of, or bacteriocin produced from, *Pseudomonas aeruginosa* bacterium, ATCC Accession No. PTA-124262 and progeny or derivatives thereof. These compositions can contain whole cell or bacteriocin from other microorganisms. Such compositions can be added together or sequentially to the aqueous systems.

Still other aspects and advantages of these compositions and methods are described further in the following detailed description of the preferred embodiments thereof.

DETAILED DESCRIPTION

Methods and compositions are described for mitigation of souring and MIC in oil and gas pipeline environments, including aqueous (water-containing) environments, as well as for other uses. Composition and methods for remediation of unwanted prokaryotes, particularly SRPs, in aqueous environments in oil and gas pipelines are provided by introduction of whole cells from a novel *Pseudomonas aeruginosa* strain ATCC PTA-124262, recovered from oil and gas operation waste waters and/or bacteriocin produced by that strain. The use of such methods and compositions are designed to reduce hydrogen sulfide production and associated souring and MIC. The exposure of oil and gas pipelines to these viable bacterial cells that produce and secrete chemicals (bacteriocins) that inhibit the growth of SRPs is a valuable tool for such remediation.

Exposure of oil and gas pipelines to the anti-SRP *Pseudomonas* strains leads to co-colonization of new and pre-existing SRP-containing biofilms along the inner surfaces of the pipelines. The close proximity between SRPs and the anti-SRP *Pseudomonas* strains induce the *Pseudomonas* strains to produce anti-SRP bacteriocins in order to achieve a competitive advantage.

Definitions and Components of the Compositions and Methods

Technical and scientific terms used herein have the same meaning as commonly understood by one of ordinary skill in the art to which this invention belongs and by reference to published texts, which provide one skilled in the art with a general guide to many of the terms used in the present application. The definitions contained in this specification are provided for clarity in describing the components and compositions herein and are not intended to limit the claimed invention. The following terms are used throughout the specification.

By "bacteriocins" is meant proteinaceous (peptide or proteins) anti-microbial toxins normally produced by bacteria to inhibit the growth of taxonomically similar microbial competitors in the nearby environment. Productions of bacteriocins both by Gram positive bacteria (such as lactic acid bacteria or *Bacillus*), and by Gram negative bacteria (many members of Enterobacteriaceae family, such as *Escherichia coli*), have been documented. Some of the documented bacteriocins exhibit a broad inhibition spectrum covering many members of Gram positive and Gram negative bacteria. The bacteriocin of ATCC Accession No. PTA-124262 inhibits growth of the SRPs, thereby reducing sulfide production and associated souring and MIC. Bacteriocins showing activity against different strains of SRPs have great potential for environmental applications as natural biocides in oil and gas industries, among others.

The term "unwanted prokaryote," as used herein, refers to single-celled organisms that do not have a nucleus or any other membrane-bound organelles, e.g., bacteria, cyanobacteria, and archaea. These prokaryotes include the strain(s) of prokaryotes, e.g., bacteria, specifically targeted for control by the invention described herein. Typically, but not necessarily, the unwanted prokaryotes are targeted for control because of interference with reactions or processes, such as in the case of unwanted SRPs and/or IRBs in oil and gas drilling and in production waters such as fracturing water, produced water and water. The unwanted prokaryotes need not necessarily be known, isolated, or identified; the sole defining characteristic is that it is the organism(s) desired to be controlled. This invention provides for reduction of invasive prokaryotes and other unwanted and problematic prokaryotes, e.g., SRPs and sulfate-reducing bacteria.

By "oil and gas field environments" or "oil and gas aqueous environments" is meant the fluids naturally occurring in the well itself or any type of fluid employed in a hydrocarbon recovery operation such as pipeline operations, well servicing operations, upstream exploration and production operations, downstream refining, processing, storage and transportation applications, and sterilization of flowback fluids. Such environments include drilling fluids, lost circulation fluids, stimulation fluids, sand control fluids, completion fluids, acidizing fluids, scale inhibiting fluids, water-blocking fluids, clay stabilizer fluids, fracturing fluids, frac-packing fluids, gravel packing fluids, wellbore strengthening fluids, acidizing fluids, sag control fluids, any flow-back fluid, which is a non-hydrocarbon containing fluid that flows from the well to the surface following treatment with another fluid, or wastewater.

By "carrier" as used herein includes, but is not limited to, aqueous-based fluids, such as fresh water, seawater, saltwater, or brine (e.g., water containing or saturated with one or more dissolved salts) and any combination thereof. A carrier may also be an aqueous-miscible fluid, such as alcohols, e.g., methanol, ethanol, n-propanol, isopropanol, n-butanol, sec-butanol, isobutanol, and t-butanol; glycerins; glycols, e.g., polyglycols, propylene glycol, and ethylene glycol; polyglycol amines; polyols; any derivative thereof; any in combination with salts, e.g., sodium chloride, calcium chloride, calcium bromide, zinc bromide, potassium carbonate, sodium formate, potassium formate, cesium formate, sodium acetate, potassium acetate, calcium acetate, ammonium acetate, ammonium chloride, ammonium bromide, sodium nitrate, potassium nitrate, ammonium nitrate, ammonium sulfate, calcium nitrate, sodium carbonate, and potassium carbonate. Combinations of one or more aqueous-miscible fluid with an aqueous-based fluid may also serve as carriers for the compositions described herein. Still other suitable carriers include emulsions, such as water-in-oil emulsions or oil-in-water emulsions, which are described in US2014/0090833, incorporated by reference herein.

By "additive" is meant pH adjuster or buffering agent, a carbon source, and glycerol, as well as any necessary reagents for cryopreservation until time of use. In one embodiment, the purified or partially purified bacteriocin is stable in just a buffer solution. In another embodiment, to stabilize a formulation containing whole cells, the formulation can include a salt, buffer to maintain pH, optionally a low level of a carbon source, and optionally glycerol.

"Effective amount" as used herein means an amount of whole cell sufficient to produce bacteriocin in sufficient concentration to cause a detectable reduction in, or killing of, targeted unwanted prokaryotes, e.g., bacteria. The effective amount can also be expressed in the amount of bacteriocin sufficient to cause a detectable reduction in, or killing of, targeted unwanted prokaryotes (e.g., SRPs). In some embodiments, the effective amount/concentration of whole cells of ATCC Accession No. PTA-124262 in the indicated oil and gas environment fluid is a concentration at least comparable to the level of SRPs present in the indicated environment. In one embodiment, an effective amount is at least $1\times10^3$, $1\times10^4$, $1\times10^5$, $1\times10^6$, $1\times10^7$, $1\times10^8$, or $1\times10^9$ colony forming units (cfu)/mL. In one embodiment, an effective amount is at least $1\times10^6$ cfu/ml. Higher or lower concentrations can also be employed. Similar amounts of other whole cell bacteria demonstrating anti-SRP activity may be combined with similar or smaller amounts of ATCC Accession No. PTA-124262, in the event of synergistic anti-SRP effect.

In some embodiments, the "effective amount" of bacteriocin in the indicated oil and gas environment fluid is an amount at least 0.1, 0.2, 0.3, 0.4, 0.5, 0.6, 0.7, 0.8, 1, 5, 10, 30, 50, 80, or 100 ppm. In one embodiment, the dose is about 1 ppm. In some embodiments, the effective amount of bacteriocin in the indicated oil and gas environment fluid is an amount at least 0.1, 1, 10, 20, 30, 40, 50, 60, 70, 80, 90, 100, 110, 120, 130, 140, 150, 160, 170, 180, 190, 200, 210, 220, 230, 240, 250, 260, 270, 280, 290 or about 300 mg/ml. Higher or lower concentrations can also be employed. Similar amounts of other bacteriocins demonstrating anti-SRP activity may be combined with similar or smaller amounts of ATCC Accession No. PTA-124262 bacteriocin, in the event of synergistic anti-SRP effect.

The phrase "anti-SRP effect" or "anti-SRP activity" means the ability to interfere with or reduce the propagation of functional SRPs. In another embodiment, anti-SRP activity means the ability to kill SRPs.

The words "comprise", "comprises", and "comprising" are to be interpreted inclusively rather than exclusively, i.e., to include other unspecified components or process steps. The words "consist", "consisting", and its variants, are to be interpreted exclusively, rather than inclusively, i.e., to exclude components or steps not specifically recited.

The terms "a" or "an" refers to one or more. For example, "an expression cassette" is understood to represent one or more such cassettes. As such, the terms "a" (or "an"), "one or more," and "at least one" are used interchangeably herein.

As used herein, the term "about" means a variability of plus or minus 10% from the reference given, unless otherwise specified.

Compositions

In one embodiment, a newly discovered strain of *Pseudomonas aeruginosa* bacteria produces a bacteriocin in situ having broad killing range for SRPs. In one embodiment, the newly isolated *P. aeruginosa* was deposited on Jun. 28, 2017 under Accession No. PTA-124262 with the American Type Culture Collection, located at 10801 University Boulevard, Manassas, VA 20110 USA. As described in the examples below, this novel Gram negative, *Pseudomonas* strain was isolated from an oil and gas environment, i.e., from oil and gas field wastewater. This strain has been shown to inhibit SRP growth in zone-of-inhibition assays on agar plates. The anti-SRP activity was found to be associated with an R-type pyocin (*Pseudomonas* bacteriocin with a bacteriophage tail structure).

In another embodiment, progeny of ATCC Accession No. PTA-124262 and/or derivatives thereof are provided and can be used in the compositions and methods described herein. By "progeny" is meant repeated generations of ATCC Accession No. PTA-124262 resulting from repeated culturing and including any mutations that occur naturally during culturing. By "derivatives" are meant progeny bacteria of the deposited microorganisms which carry mutations or deletions of amino acids or nucleotide bases which are created in the bacterial genome by genetic engineering or recombinant manipulation techniques.

In one embodiment, ATCC Accession No. PTA-124262 and progeny or derivatives carry naturally occurring or genetically manipulated proteins including tail fiber and tail tube proteins. The anti-SRP bacteriocin produced by ATCC Accession No. PTA-124262 is an R-type pyocin with the structure of a phage tail. The complex consists of about 130 copies of a FI tail sheath monomer SEQ ID NO: 3, with a length of 386 AA and a predicted weight of 41 kDa, and about 130 copies of a FII tail tube monomer SEQ ID NO: 4 with a length of 167 AA and a predicted weight of 18 kDa. The approximate predicted molecular weight of the entire pyocin is 7700 kDa. The anti-SRP activity of the bacteriocin is associated with the particular three dimensional structure/interaction of the associated tail fiber proteins. Altering these sequences is anticipated to alter or broaden the specificity of the bacteriocin. The tail fiber proteins SEQ ID NO: 1 and 2 are present at low copy number. The tail fiber proteins are involved in binding of the pyocin to a target cell, i.e. host range specificity. The major structural proteins aren't directly involved in host recognition.

Amino acid sequences for the two major structural proteins and two of the tail fiber proteins of the ATCC Accession No. PTA-124262 anti-SRP bacteriocin are:

```
contig00021_64327_64860 Phage tail fibers ~20 kDa:
                                              SEQ ID NO: 1
MSSRLLPPNRSSLERSLGDVLPAELPVPLRELNDPARCEAALLPYLAWTR

SVDRWDPDWSDEAKRNAVATSFVLHQRKGTLTALRQVVEPIGALSEVTEW

WQRSPLGVPGTFEITVDVSDRGIDEGTVLELERLLDDVRPVSRHLTRLDL

RITPVIRSRHGLAVTDGDTLEIFPWKQ contig00021_64862_66967 Phage tail fiber protein
~73 kDa
                                              SEQ ID NO: 2
MTTNTPKYGGLLTDIGAAALAAASAAGKKWQPTHMLIGDAGGAPGDTPDP

LPSAAQKSLINQRHRAQLNRLFVSDKNANTLVAEVVLPVEVGGFWIREIG

LQDADGKFVAVSNCPPSYKAAMESGSARTQTIRVNIALSGLENVQLLIDN

GIIYATQDWVKEKVAADFKGRKILAGNGLVGGGDLSADRSIGLAPSGVTA

GSYRSVTVNANGVVTQGSNPTTLAGYAIGDAYTKADTDGKLAQKANKATT

LAGYGITDALRVDGNAVSSSRLAAPRSLAASGDASWSVTFDGSANVSAPL

SLSATGVAAGSYPKVTVDTKGRVTAGMALAATDIPGLDASKLVSGVLAEQ

RLPVFARGLATAVSNSSDPNTATVPLMLTNHANGPVAGRYFYIQSMFYPD

QNGNASQIATSYNATSEMYVRVSYAANPSIREWLPWQRCDIGGSFTKTTD

GSIGNGVNINSFVNSGWWLQSTSEWAAGGANYPVGLAGLLIVYRAHADHI

YQTYVTLNGSTYSRCCYAGSWRPWRQNWDDGNFDPASYLPKAGFTWAALP

GKPATFPPSGHNHDTSQITSGILPLARGGLGANTAAGARNNIGAGVPATA

SRALNGWWKDNDTGLIVQWMQVNVGDHPGGIIDRTLTFPIAFPSACLHVV

PTVKEVGRPATSASTVTVADVSVSNTGCVIVSSEYYGLAQNYGIRVMAIG

Y contig00021_67458_68618 Phage tail sheath monomer
(FI tail sheath) ~41 kDa (~130 copies per tail)
                                              SEQ ID NO: 3
MSFFHGVTVTNVDIGARTIALPASSVIGLCDVFTPGAQASAKPNVPVLLT

SKKDAAAAFGIGSSIYLACEAIYNRAQAVIVAVGVEAAETPEAQASAVIG

GVSAAGERTGLQALLDGKSRFNAQPRLLVAPGHSAQQAVATAMDGLAEKL
```

-continued

RAIAILDGPNSTDEAAVAYAKNFGSKRLFMVDPGVQVWDSATNAARNAPA

SAYAAGLFAWTDAEYGFWSSPSNKEIKGVTGTSRPVEFLDGDETCRANLL

NNANIATIIRDDGYRLWGNRTLSSDSKWAFVTRVRTMDLVMDAILAGHKW

AVDRGITKTYVKDVTEGLRAFMRDLKNQGAVINFEVYADPDLNSASQLAQ

GKVYWNIRFTDVPPAENPNFRVEVTDQWLTEVLDVA

```
contig00021_68631_69134 Phage major tail tube
protein (FII tail tube) ~18 kDa (~130 copies per
tail)
                                         SEQ ID NO: 4
```
MIPQTLTNTNLFIDGVSFAGDVPSLTLPKLAVKTEQYRAGGMDAPVSIDM

GLEAMEAKFSTNGARREALNFFGLADQSAFNGVFRGSFKGQKGASVPVVA

TLRGLLKEVDPGDWKAGEKAEFKYAVAVSYYKLEVDGREVYEIDPVNGVR

AINGVDQLAGMRNDLGL

Such proteins may be genetically manipulated or engineered to result in certain mutated proteins having desirable characteristics. Thus, proteins produced by the progeny and derivatives of ATCC Accession No. PTA-124262 include naturally occurring proteins, such as SEQ ID Nos 1-4, encoded by the genomic DNA or cDNA derived from the microorganism, as well as functional proteins (i.e., proteins that demonstrate the biological activity of the normally functioning protein SEQ ID Nos: 1, 2, 3 and/or 4, with mutations or modifications of its encoding DNA sequence or within its amino acid sequence. In another embodiment, such a functional protein can include mutations which cause the protein to perform its anti-SRP functions better than a "native" or endogenous sequence. In one embodiment, such a functional bacteriocin or one of its individual protein elements can be considered a normal or normally-functioning protein.

Also included in the use of the definitions of the bacteriocin protein and tail fiber proteins described herein include sequences which differ from the reference sequences SEQ ID NO: 1, 2, 3 and/or 4 by virtue of naturally occurring nucleic acid base or amino acid mutations or silent mutations that occur in, or among, a selected species, or amino acid sequences which differ by conservative amino acid replacements, or sequences having at least 90, at least 95 or at least 99 percent identity with the reference sequences SEQ ID NO: 1, 2, 3 and/or 4.

Thus, in one embodiment, the tail fiber or bacteriocin protein sequences of ATCC Accession No. PTA-124262 and progeny or derivatives include a variant which shares or comprises at least 70, at least 75%, at least 78% or at least 80% identity with SEQ ID NO: 1, 2, 3 or 4. In another embodiment, the tail fiber or bacteriocin protein sequences share at least 85% identity with a native protein produced by these bacteria. In another embodiment, the bacteriocin or tail fiber protein sequence shared at least 90% identity with a native bacteriocin or tail fiber protein sequence (i.e., SEQ ID NO: 1, 2, 3 or 4). In another embodiment, the bacteriocin or tail fiber protein(s) sequence shares at least 91% identity with a native bacteriocin or tail fiber protein(s). In another embodiment, the bacteriocin or tail fiber protein(s) sequence shares at least 92% identity with a native bacteriocin or tail fiber protein(s). In another embodiment, the bacteriocin or tail fiber protein(s) sequence shares at least 93% identity with a native bacteriocin or tail fiber protein(s). In another embodiment, the bacteriocin or tail fiber protein(s) sequence shares at least 94% identity with a native bacteriocin or tail fiber protein(s). In another embodiment, the bacteriocin or tail fiber protein(s) sequence shares at least 95% identity with a native bacteriocin or tail fiber protein(s). In another embodiment, the bacteriocin or tail fiber protein(s) sequence shares at least 96% identity with a native bacteriocin or tail fiber protein(s). In another embodiment, the bacteriocin or tail fiber protein(s) sequence shares at least 97% identity with a native bacteriocin or tail fiber protein(s). In another embodiment, the bacteriocin or tail fiber protein(s) sequence shares at least 98% identity with a native bacteriocin or tail fiber protein(s). In another embodiment, the bacteriocin or tail fiber protein(s) sequence shares at least 99% identity with a native bacteriocin or tail fiber protein(s) described herein. In a similar manner, the nucleotide sequences encoding the bacteriocin or tail fiber protein(s) of ATCC Accession No. PTA-124262 and its progeny or derivatives may share analogous percent identities over a stretch of contiguous nucleotide bases encoding the proteins.

The terms "percent (%) identity", "sequence identity", "percent sequence identity", or "percent identical" in the context of amino acid sequences refers to the residues in the two sequences which are the same when aligned for correspondence. Percent identity may be readily determined for amino acid sequences over the full-length of a protein, polypeptide, about 10 amino acids to about 300 amino acids, or a peptide fragment thereof. Percent identity may be readily determined for nucleotide sequences over the full-length nucleic acid sequence coding sequences or partial coding sequences, or non-coding sequences.

Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another method which provides at least the same level of identity or alignment as that provided by the referenced methods. See, e.g., J. D. Thomson et al, Nucl. Acids. Res., "A comprehensive comparison of multiple sequence alignments", 27(13):2682-2690 (1999).

The bacteriocin or tail fiber protein(s) of the deposited microorganism or its progeny or derivatives may also be "optimized" or "codon-optimized". The bacteriocin or tail fiber protein(s) can be encoded by a DNA sequence which differs from the native or naturally occurring sequence, such as that of SEQ ID NO: 1, 2, 3 or 4, by codon changes that make silent, conservative or non-conservative amino acid changes, or amino acid insertions or deletions in the protein(s). These changes may increase protein production and/or enhance protein conformation and stability. Synonymous codon changes or codon changes resulting in conservative amino acid changes, or insertions or deletions can increase protein production and/or enhance protein conformation and stability.

Creating bacteriocins or tail fiber proteins that differ from the native sequences can be accomplished by various different methods. Optimization may be performed using methods which are available on-line, published methods, or a company which provides codon optimizing services (see e.g., in International Patent Application Pub. No. WO 2015/012924, which is incorporated by reference herein). Briefly, the nucleic acid sequence encoding the desired protein is modified with synonymous codon sequences. Suitably, the entire length of the open reading frame (ORF) for the bacteriocin or tail fiber protein(s) is modified. However, in some embodiments, only a fragment of the ORF may be altered. By using one of these methods, one can produce a nucleic acid fragment of a codon-optimized coding region which encodes the bacteriocin or tail fiber protein. Such modifications or synthesis of bacteriocins and/or tail fiber proteins can be performed using standard and routine molecular biological manipulations well known to those of ordinary skill in the art. See, Green and Sambrook et al, "Molecular Cloning. A Laboratory Manual", Fourth Edition, 2012 by Cold Spring Harbor Laboratory Press, Cold Spring Harbor, New York, among other texts.

It is anticipated that several other gene products are required for full transcription, assembly, function and specificity of the anti-SRP bacteriocin.

Compositions described herein, in one embodiment, have broad range killing activity against SRPs and comprise, in one embodiment, whole cell *Pseudomonas aeruginosa* bacterium, ATCC Accession No. PTA-124262 and progeny or derivatives thereof and a suitable carrier. In another embodiment, such a composition can also include at least one or more additional bacteria that is or are useful in reducing corrosion or souring. Among such bacteria include other strains of *Pseudomonas aeruginosa*. In another embodiment strains of *Thauera aminoaromatica* may be included in the composition. In still another embodiment, strains of the bacteria *Ideonella* may be employed. Still other bacteria known or found to produce anti-SRP bacteriocins or to compete with IRBs, APBs, and the like present in oil and gas field environments may be combined with ATCC Accession No. PTA-124262 in a suitable composition. Other known bacterial strains known by the art to be suitable for anti-souring and anti-corrosion effect may also be added to the compositions described herein.

In still another embodiment, the compositions containing ATCC Accession No. PTA-124262 may also contain additional suitable bacteriocin protein(s) rather than additional whole cell bacteria, for such use. See, e.g., the bacteriocin described in US published patent application No. 2014/0090833, incorporated by reference herein.

Compositions having broad range killing activity against SRPs comprise, in another embodiment, a bacteriocin produced from the bacterium ATCC Accession No. PTA-124262 and progeny or derivatives thereof as described above, and a suitable carrier. In another embodiment, such a composition can also include at least one or more additional bacteriocin(s) that is/are useful in reducing corrosion or souring. Among such bacteriocins are included those produced by other strains of *Pseudomonas aeruginosa*, such as pyocin R1, R2, R3, R4, S1, S2, S3, S4, S5, F1, F2, F3, AP41, and AR41, which may have anti-corrosion or anti-SRP activity. In another embodiment strains of *Thauera aminoaromatica* may be included in the composition. In still another embodiment, bacteriocin produced by strains of the bacteria *Ideonella* may be employed. Still other bacteriocins known to be toxic to IRBs, APBs, and the like present in oil and gas field environments may be combined with the bacteriocin produced by ATCC Accession No. PTA-124262 in a suitable composition. Other known bacteriocins known by the art to be suitable for anti-souring and anti-corrosion effect may also be added to the compositions described herein, such as those described in US published patent application No. 2014/0090833, incorporated by reference herein. Other bacteria or bacteriocins isolated therefrom having a corrosion protective potential may be employed in concert with whole cell bacterium ATCC Accession No. PTA-124262 and progeny or derivatives thereof, including without limitation, *Bacillus thuringiensis*-SN8 (Bano, Arjumand Shah, and Javed Iqbal Qazi. "Soil buried Mild Steel Corrosion by *Bacillus cereus*-SNB4 and its Inhibition by *Bacillus thuringiensis*-SN8." Pakistan J. Zool 43.3 (2011): 555-562.); *Bacillus subtilis*-LFE-1, *Bacillus firmus*-H2O-1 and *Bacillus licheniformis*-T6-5 (Korenblum, E., et al. "Production of antimicrobial substances by *Bacillus subtilis* LFE-1, *B. firmus* H2O-1 and *B. licheniformis* T6-5 isolated from an oil reservoir in Brazil." Journal of Applied Microbiology 98.3 (2005): 667-675.); *Bacillus* sp. H2O-1 (Korenblum, Elisa, et al. "Purification and characterization of a surfactin-like molecule produced by *Bacillus* sp. H2O-1 and its antagonistic effect against sulfate reducing bacteria." BMC microbiology 12.1 (2012): 252.).

In one embodiment, such whole cell ATCC Accession No. PTA-124262 only may be prepared for use in one or more of the carriers described and defined above for a variety of uses. In another embodiment, mixtures of ATCC Accession No. PTA-124262 with such other bacteria as mentioned above may be prepared for use in one or more of the carriers described and defined above for a variety of uses. In another embodiment, mixtures of ATCC Accession No. PTA-124262 cells with bacteriocin produced by the other above-mentioned bacteria may be prepared for use in one or more of the carriers described and defined above for a variety of uses. In still another embodiment bacteriocin and/or tail fiber protein (s) produced by and isolated from ATCC Accession No. PTA-124262, which may be mutated or modified as described above, may be prepared for use in one or more of the carriers described and defined above for a variety of uses. In another embodiment, mixtures of the bacteriocin of ATCC Accession No. PTA-124262 (naturally occurring and/or modified as described above) with other bacteriocins produced by other bacteria, may be prepared for use in one or more of the carriers described and defined above for a variety of uses. In still a further embodiment, mixtures of whole cell ATCC Accession No. PTA-124262 with its own or other bacteriocin compositions may be prepared for use in one or more of the carriers described and defined above for a variety of uses.

Such whole cell, bacteriocin or mixed whole cell and bacteriocin may be added to compositions for use or measured in situ in concentrations suitable to achieve their anti-SRP, anti-souring, anti-corrosion effect, as also defined herein.

Methods

The anti-SRP activity of *P. aeruginosa* ATCC Accession No. PTA-124262 is useful in diminishing the SRP population in mixed biofilms in which it is present. It is theorized that ATCC Accession No. PTA-124262 is an oilfield isolate that may have existed in close proximity to SRPs in the oilfield; and that bacteriocins are produced by bacteria to diminish other bacterial populations that exist in close proximity and that compete for the same/similar carbon sources (i.e. both can use lactate). Many bacteria in the environment exist within multi-species biofilm formations.

Treatment of pipelines and other oil and gas field environments, within oil drilling and natural gas fracking operations, with whole-cell ATCC Accession No. PTA-124262 co-colonizes new or pre-existing SRP-containing biofilms with an organism that has the effect of diminishing the SRP population within the biofilm. While complete biofilm dispersal may or may not occur during treatment, sulfide production is reduced, thereby reducing the risk of souring and MIC.

In one embodiment, the whole-cell *P. aeruginosa* ATCC Accession No. PTA-124262 compositions described herein having anti-SRP functionality, represent an inexpensive, differentiated technology that is not expected to encounter difficult regulatory hurdles.

Thus, in one embodiment, a method of controlling prokaryotes in an oil or gas field environment or treatment fluid, as defined above, comprises contacting the selected environment with an amount of *Pseudomonas aeruginosa* bacterium, ATCC Accession No. PTA-124262 and progeny or derivatives thereof effective to produce bacteriocin in situ which is virulent for the unwanted prokaryotes. The contacting occurs for a time sufficient to permit the bacterium to produce bacteriocin virulent for the unwanted prokaryotes or for the bacteriocin to kill the unwanted prokaryotes. As described above, the unwanted prokaryotes are SRPs, including without limitation one or more of *D. alaskensis, D. desulfuricans, D. longus*, or *D. vulgaris*. The method further comprises optionally contacting the selected oil and gas field environment with whole cell bacteria of another strain of *Pseudomonas aeruginosa*, or *Thauera aminoaromatica* or *Ideonella* that are capable of killing SRP.

In another embodiment, a method of controlling unwanted prokaryotes in an oil or gas field environment or treatment fluid, as defined above, comprises contacting the selected environment with an amount of a bacteriocin produced by *Pseudomonas aeruginosa* bacterium, ATCC Accession No. PTA-124262 and progeny or derivatives thereof. The bacteriocin are provided in effective amounts to be virulent for, reduce the number of, or kill, the unwanted prokaryotes. The method permits the bacteriocin virulent for the unwanted prokaryotes or for the bacteriocin to kill or substantially reduce the growth of the unwanted prokaryotes. As described above, in certain embodiments, the unwanted prokaryotes are SRPs, such as one or more of *D. alaskensis, D. desulfuricans, D. longus*, or *D. vulgaris*. The method further comprises optionally contacting the selected oil and gas field environment with bacteriocin produced by bacteria of another strain of *Pseudomonas aeruginosa*, or *Thauera aminoaromatica* or *Ideonella* that are capable of killing SRP.

In still further embodiments, the methods of reducing or controlling unwanted bacteria in oil and gas field environments comprises adding an effective amount of such whole cell ATCC Accession No. PTA-124262 only, or mixtures of ATCC Accession No. PTA-124262 with other bacteria, or bacteriocin only produced by and isolated from ATCC Accession No. PTA-124262, or mixtures of the bacteriocin of ATCC Accession No. PTA-124262 with other bacteriocins produced by other bacteria, or mixtures of whole cell ATCC Accession No. PTA-124262 with its own or other bacteriocin compositions as described herein to any oil or gas field environment or fluid.

The embodiment of the methods described herein use whole cell ATCC Accession No. PTA-124262 as a self-propagating biopesticide. These methods do not require costly bacteriocin purification. The use of the whole cell ATCC Accession No. PTA-124262 specifically targets SRPs (souring and MIC), without the need for added chelating agents, surfactants, etc. The whole cell method described herein represents a natural alternative that provides targeted biocontrol of MIC. From a regulatory perspective, use of the whole cell culture as a biopesticide is likely to be considered safer than chemical biocides. In one embodiment, the whole-cell bacterial treatment takes the form of a native, environmental isolate that has not undergone any genetic engineering. In addition, the biopesticidal activity propagates within the pipeline as a result of the propagation of the producing organism ATCC Accession No. PTA-124262.

Without being bound by theory, these methods exploit the strong tendency of microorganisms to exist within mixed biofilms in the environment. It is hypothesized that, although *Pseudomonas* ATCC Accession No. PTA-124262 and SRPs are not very similar taxonomically, this isolate produces an anti-SRP bacteriocin because it co-existed with SRPs in the oilfield environment and evolved an anti-SRP bacteriocin as a self-defense mechanism. While the trigger for turning on the bacteriocin expression is unknown, it is hypothesized that co-colonization of a biofilm by ATCC Accession No. PTA-124262 and SRPs promotes production or over-production of the anti-SRP bacteriocin.

In addition to the method steps defined above, other methods used in oil and gas operations to remediate unwanted prokaryotes that cause fouling, corrosion and reservoir souring (H2S production) may also employ the compositions containing ATCC Accession No. PTA-124262 or its bacteriocin described herein. A variety of suitable methods are described in U.S. Pat. No. 8,168,419 issued May 1, 2012 and U.S. 8,252,576, issued Aug. 28, 2012, the disclosures of which are incorporated herein by reference.

The compositions containing ATCC Accession No. PTA-124262 or its bacteriocin may be added to bacteriophage as well as other biocides. Since the bacteria in oil and gas wells are diverse, the remediation of a dominant strain may allow a less dominant strain to become dominant. In such case the less dominant may not be killed by the initially applied biocide composition (cocktail) used so that the cocktail composition is changed to remediate the dynamic changing population of unwanted prokaryotes. The change is effected base on monitored analysis or timed sequence.

A method of accomplishing such dynamic behavior is described in U.S. published application 2014/0273159, published, Sep. 18, 2014, for staged bacteriophage. The same procedures and methods may be applied for the composition (whole cell or bacteriocin or mixed) described herein. The whole cell ATCC Accession No. PTA-124262 or its bacteriocin may be contained in cocktails with bacteriophage including those described in U.S. published application 2014/0273159, published Sep. 18, 2014, the disclosure of which is incorporated herein by reference.

In one embodiment, a process for control of a broad range of target bacteria comprises culturing a dominant group of bacteria in a mixed bacteria solution. A composition containing ATCC Accession No. PTA-124262 which produces its bacteriocin in situ, or a composition containing the bacteriocin isolated from ATCC Accession No. PTA-124262 as well as other additional whole cell bacterial strains (e.g., *Pseudomonas aeruginosa, Thauera aminoaromatica* and *Ideonella*) and/or bacteriocin isolated therefrom are added to remove the dominant bacteria from the mix. The next dominant strain is cultured from the solution. An effective amount of whole cell ATCC Accession No. PTA-124262 and its bacteriocin with or without other bacteria or isolated bacteriocins from other bacterial strains is thereafter added to remove the next dominant bacteria. This series of steps is repeated to provide a set of ATCC Accession No. PTA-124262 progeny or derivatives thereof, and/or isolated bacteriocin that will reduce the dominant and sub-dominant bacteria. An effective amount of the ATCC Accession No. PTA-124262 progeny or derivatives or bacteriocin produced thereby that is/are so isolated in each step is thereafter applied as either a mixture or in sequential application to oil and gas field environments or treatment fluids containing a mixture of target bacteria of those found in each step of the above sequence.

It is further anticipated that the novel ATCC Accession No. PTA-124262 or its bacteriocin may be used for microbial control in environments, fluids and industries other than oil and gas production, e.g., for wastewater treatment in other contexts or even as additives to other products requiring microbial control.

EXAMPLES

The following examples disclose specific embodiments of the methods and compositions and should be construed to encompass any and all variations that become evident as a result of the teaching provided herein.

Example 1: Screening for Strains Producing Antimicrobial Substances Against Oil Field SRP Several thousand bacterial strains isolated from up to one hundred oil and gas samples were screened for their capabilities to produce substances that kill SRPs. The oil and gas samples include fracturing water, produced water, pit water, waste water collected mainly from North American production plants (oil and gas water systems). In detail, these samples were serial diluted and plated onto SRP selecting media plates. After incubation, the grown up individual colonies were picked and transferred onto a fresh plate. The colony leftovers on the original plate were killed by chloroform vapor.

The killed plates were overlaid with indicator bacterial lawns freshly made with different SRPs, including *D. alaskensis, D. desulfuricans, D. longus, D. vulgaris* and EBS.14 (a field isolate from Barnett Shale). After incubation, any zone of inhibition (ZOI) on the indicator SRP lawns was noted and the matching copy of the producing strain (transferred on a separate plate before killing) was purified and identified. ATCC Accession No. PTA-124262 was evaluated by 16S rDNA sequencing as *Pseudomonas aeruginosa*. The antimicrobial substance produced by this strain showed broad killing spectrum against 34 of 45 different SRP strains isolated from oil and gas fields.

Example 2: Preparation of Bacteriocin Extract from *Pseudomonas Aeruginosa* EC42.15

A single colony of *Pseudomonas aeruginosa* EC42.15 ATCC Accession No. PTA-124262 was inoculated into 10 mL tryptic soy broth (TSB) and the culture was incubated overnight at 30° C. with shaking at 50 rpm. An aliquot of the overnight culture was transferred into a larger volume of TSB, using a 2% (v/v) inoculation level. The larger culture was incubated (30° C., 50-100 rpm) and the culture density was monitored until an $OD_{600}$ of about 0.4 was reached. Mitomycin C was then added to the culture to a final level of 1 µg/mL. Incubation (30° C., 50 rpm) was continued for an additional 18 hrs. Cells were collected by centrifugation at 11,000×g. The clarified supernatant (bacteriocin extract) was sterile-filtered and refrigerated.

The anti-SRP activity of the bacteriocin extract was partially purified using an ultrafiltration unit. The bacteriocin extract was passed through a 300 kDa molecular weight cut-off membrane, while stirring under an external pressure of 10 psi nitrogen. Ultrafiltration continued until the retentate volume was 10% of the starting volume. The retentate, which contained the anti-SRP activity, was desalted by diluting to the original volume in 10 mM Tris-Cl, pH 7.5, and repeating the concentration step. The partially purified bacteriocin extract was stored refrigerated.

Example 3: Characterization and Production of the Antimicrobial Substances Produced by *P. Aeruginosa* ATCC Accession No. PTA-124262

The genome of *P. aeruginosa* ATCC Accession No. PTA-124262 was sequenced. The complete bioinformatics analysis of the genome sequence identified DNA regions coding putative antimicrobial proteins, SEQ ID Nos: 1, 2, 3 and 4. These antimicrobial proteins were partially purified from the culture supernatant and the specific activity against SRPs was determined as described above. It is anticipated that further modification of these proteins will permit efficient production for application in controlling SRP of oil and gas industries. The antimicrobial proteins can be expressed in their native host, i.e., ATCC Accession No. PTA-124262, or expressed in a different bacterial host for maximum production rate. Multiple antimicrobial proteins with different SRP killing spectrums can be combined for broader SRP control in the oil and gas industry.

The bacteriocin of ATCC Accession No. PTA-124262 is an R-type pyocin with a phage tail structure. The complex consists of about 130 copies of a FI tail sheath monomer SEQ ID NO: 3, with a length of 386 AA and a predicted weight of 41 kDa, and about 130 copies of a FII tail tube monomer SEQ ID NO: 4 with a length of 167 AA and a predicted weight of 18 kDa. The approximate predicted molecular weight of the entire pyocin is 7700 kDa. The estimate of expression level of the R-type pyocin in induced culture was 10 mg/L. The bacteriocin produced by ATCC Accession No. PTA-124262 was effective in producing a zone of inhibition, showing bioefficacy against *D. alaskensis* in the sub-nanomolar range, i.e., on a plate at a level of 1 ppm.

Example 4: Analysis of the Effect of Whole Cell *Pseudomonas Aeruginosa* EC42.15 ATCC Accession No. PTA-124262 on the Viability of *Desulfovibrio Alaskensis* ATCC 14563

The viability of *D. alaskensis* ATCC 14563 was monitored in the presence of *P. aeruginosa* EC42.15 (ATCC Accession No. PTA-124262). As a control, the viability of *D. alaskensis* ATCC 14563 was also monitored in the presence of *P. aeruginosa* (ATCC Accession No. 15442), which is a *P. aeruginosa* strain that does not produce a bacteriocin that is active against *D. alaskensis*. All experiments were conducted in an anaerobic chamber, and all incubations were done at 30° C.

Stock cultures of *P. aeruginosa* ATCC Accession No. PTA-124262 and ATCC Accession No. 15442 were prepared in TSB amended with 1% (w/v) potassium nitrate (TSB-N). Stock cultures of *D. alaskensis* were prepared in ATCC® Medium 1250: Modified Baar's Medium for Sulfate Reducers with NaCl (2.5% w/v) (MB-1250). The media used for testing the effect of the *P. aeruginosa* strains on the viability of *D. alaskensis* consisted of a 1:1 mixture of the two medias noted above. *P. aeruginosa* was enumerated by observing turbidity in 96-well plates containing TSB-N. This medium also allowed for selective enumeration of *P. aeruginosa* from mixtures of this strain with *D. alaskensis. D. alaskensis* was enumerated by observing iron sulfide precipitation in 96-well plates containing MB-1250 with iron indicator. This medium also allowed for selective enumeration of *D. alaskensis* from mixtures of this strain with *P. aeruginosa*.

Test samples were prepared by inoculating aliquots of the 1:1 media with 1% (v/v) *P. aeruginosa* alone, 1% (v/v) *D. alaskensis* alone or 1% (v/v) each of *P. aeruginosa* and *D. alaskensis*. All test samples were enumerated for both *P. aeruginosa* and *D. alaskensis* at selected time points. The data are summarized in Table I. The dose of the whole bacteriocin-producing cells is comparable to the level of sulfate-reducing bacteria present, or $\sim 1 \times 10^6$ cfu/mL.

TABLE I

| | Single Cultures | | | Co-Cultures | | | |
|---|---|---|---|---|---|---|---|
| | *P. aeruginosa* strains alone | | *D.* | *P. aeruginosa* strains + *D. alaskensis* | | *D. alaskensis* + *P. aeruginosa* strains | |
| Time (hrs) | EC42.15 ATCC PTA-124262 | ATCC 15422 | alaskensis alone ATCC 14563 | EC42.15 ATCC PTA-124262 | ATCC 15422 | EC42.15 ATCC PTA-124262 | ATCC 15422 |
| | cfu/mL (Study #1) | | | | | | |
| 0 | 6.4E+06 | — | 6.4E+05 | 5.6E+06 | — | 5.6E+05 | — |
| 4 | 2.4E+06 | — | 2.4E+06 | 5.2E+06 | — | 5.2E+06 | — |
| 24 | 7.7E+07 | — | 5.6E+06 | 7.7E+07 | — | 5.6E+03 | — |
| 48 | 7.7E+07 | — | 5.6E+06 | 7.7E+07 | — | 5.6E+05 | — |
| | cfu/mL (Study #2) | | | | | | |
| 0 | 3.0E+05 | 4.3E+07 | 1.6E+05 | — | — | — | — |
| 4 | 3.2E+07 | 6.1E+07 | 1.4E+05 | 2.6E+07 | 6.1E+07 | 1.3E+05 | 2.4E+05 |
| 24 | 6.1E+07 | 6.1E+07 | 3.3E+06 | 6.1E+07 | 6.1E+07 | 5.2E+03 | 1.8E+04 |
| 48 | 6.1E+07 | 6.1E+07 | 1.6E+06 | 6.1E+07 | 6.1E+07 | 7.6E+02 | 4.3E+07 |
| 192 | 6.1E+07 | 3.3E+07 | 6.1E+07 | 6.1E+07 | 6.1E+07 | 1.3E+06 | 7.3E+06 |

These data demonstrate decreased viability of the *D. alaskensis* SRP strain when it is cultured in the presence of *P. aeruginosa* ATCC PTA-124262.

Each and every patent, patent application, and publication, including websites cited throughout specification are incorporated herein by reference. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

The invention claimed is:

1. A partially purified supernatant extract comprising a bacteriocin from an isolated *Pseudomonas aeruginosa* bacterium, ATCC Accession No. PTA-124262 and progeny or derivatives thereof, said bacteriocin having anti-sulfate reducing prokaryote activity.

2. The partially purified supernatant extract of claim 1, wherein said derivatives are characterized by naturally occurring or genetically manipulated mutations.

3. The partially purified supernatant extract of claim 1, comprising a protein sequence of SEQ ID NO: 1, 2, 3 or 4.

4. A composition having broad range killing activity against sulfate reducing prokaryotes (SRP) comprising
the partially purified supernatant extract according to claim 1 and a suitable carrier, wherein the bacteriocin is present in an effective amount against sulfate reducing prokaryotes.

5. The composition according to claim 4, further comprising at least one additional bacteriocin from an additional bacterium.

6. The composition according to claim 5, wherein said additional bacterium is another strain of *P. aeruginosa*, or a *Thauera aminoaromatica*, or an *Ideonella*, or admixtures thereof.

7. The composition according to claim 4, further comprising other bacteriocins having anti-SRP or anti-corrosive activity.

8. The composition according to claim 4, wherein the carrier comprises an aqueous based fluid or aqueous miscible fluid.

9. The composition according to claim 8, wherein the carrier is water, salt-water, or buffered water.

10. The composition according to claim 4, wherein the composition is an oil or gas field environment or treatment fluid.

11. The composition according to claim 4, wherein the partially purified supernatant extract according to claim 1 comprises a protein sequence of SEQ ID NO: 1, 2, 3 or 4.

* * * * *